United States Patent [19]
Gerhard

[11] Patent Number: 5,517,988
[45] Date of Patent: May 21, 1996

[54] METHOD FOR DETECTING AN IRREGULAR STATE IN A NON-INVASIVE PULSE OXIMETER SYSTEM

[75] Inventor: Klamser Gerhard, Grafenau, Germany

[73] Assignee: Hewlett-Packard Company, Palo Alto, Calif.

[21] Appl. No.: 308,381

[22] Filed: Sep. 19, 1994

[30] Foreign Application Priority Data

Dec. 11, 1993 [EP] European Pat. Off. ............. 93120013

[51] Int. Cl.⁶ ........................................................ A61B 5/00
[52] U.S. Cl. ............................................ 128/633; 356/41
[58] Field of Search ................................ 128/633; 356/41

[56] References Cited

U.S. PATENT DOCUMENTS

| | | | |
|---|---|---|---|
| 4,714,341 | 12/1987 | Hamaguri et al. | 128/633 |
| 4,776,339 | 10/1988 | Schreiber | 128/633 |
| 5,152,296 | 10/1992 | Simons | 128/633 |
| 5,253,645 | 10/1993 | Friedman et al. | 128/633 |
| 5,368,026 | 11/1994 | Swedlow et al. | 128/633 |
| 5,368,224 | 11/1994 | Richardson et al. | 128/633 |

FOREIGN PATENT DOCUMENTS

9403102  2/1994  WIPO .................... 128/633

*Primary Examiner*—Angela D. Sykes
*Assistant Examiner*—Eric F. Winakur

[57] ABSTRACT

A method and an apparatus enable detection of an irregular state in a non-invasive pulse oximeter system. The system comprises an oxygen saturation sensing probe for generating spectrophotometric signals and an oxygen saturation computing section for deriving arterial hemoglobin oxygen saturation from the spectrophotometric signals. Irregular states of the system are detected by pre-defining at least one criterion for distinguishing between spectrophotometric signals indicative of the normal state of the system and spectrophotometric signals generated by the pulse oximeter system when a predetermined non-physiological event occurs. Then it is judged whether the actual spectrophotometric signals fulfill this criterion. The presence of the irregular state is detected if the actual criterion fulfill the criterion.

6 Claims, 5 Drawing Sheets

METHOD FOR DETECTING AN IRREGULAR STATE IN A NON-INVASIVE PULSE OXIMETER SYSTEM

BACKGROUND OF THE INVENTION

This invention relates generally to a non-invasive system for monitoring the arterial oxygen saturation and more particularly to a method of detecting an irregular state in a non-invasive pulse oximeter system and to a method of suppressing a pulse alarm caused by a non-physiological event in a non-invasive pulse oximeter system for measuring the arterial hemoglobin oxygen saturation.

Nowadays, the hemoglobin oxygen saturation of arterial blood is often measured with a non-invasive technique, which is called pulse oximetry. Pulse oximeters measure the arterial oxygen saturation of hemoglobin using two different monochromatic light sources, which are typically formed by LEDs, one of them emitting light in the red wavelength range of about 645 nm, the other one emitting light in the infrared wavelength range of 940 nm. The light emitted by both LEDs is transmitted through a predetermined area of the patient's body. Typically, pulse oximeter systems utilize an oxygen saturation sensing probe which is arranged to be secured to the patient's finger. Usually, the probe has the form of a clip including both light emitting diodes and a light detector. The probe is arranged such that the light of both light emitting diodes having passed the predetermined area of the patient's body is received by a single light detector. As it is known in the art of pulse oximetry, the light of both light sources is attenuated by static and dynamic absorbers on its path through the patient's body to the light detector. The arterial blood whose quantity varies with the time synchronously with the patient's heartbeat represents the only dynamic absorber during the pulse period. All other absorbers, such as skin, tissue or bone, are not time-variant. As mentioned earlier, the light detector, which may have the form of a photodiode, receives the modulated light intensities of each wavelength. Then, these signals are amplified, low pass filtered, converted from analog to digital and further processed in a microprocessor system. A pulse finding algorithm analyses the received signals, which are so-called spectrophotometric signals for identifying the pulses and for determining the pulse. After identifying the pulse period, the microprocessor system determines the diastolic and systolic values of the spectrophotometric signals and derives therefrom the so-called relative absorption ratios. Subsequently, the microprocessor system computes the arterial oxygen saturation from the relative absorption ratio using calibration data and so-called extinction coefficients from the absorption spectrum of hemoglobin and oxyhemoglobin at the appropriate wavelengths. The pulse finding algorithm of the pulse oximeter will generate an alarm if no pulsation is detectable on the spectrophotometric signals.

Typically, non-invasive systems for monitoring the arterial oxygen saturation are also used for monitoring the patient's blood pressure. The blood pressure is monitored by utilizing an inflatable blood pressure cuff which can be wrapped about the patient's limb. The monitor determines the patient's systolic and diastolic blood pressure. In some specific medical applications, it is not possible to measure the blood pressure on one arm of the patient and to detect the oxygen saturation with a probe secured to the patient's finger of the other arm. Thus, if both the pressure cuff and the oxygen saturation probe are to be used on the same arm, a measurement of the blood pressure by, for example, inflating the cuff and conducting oscillometric measurements, will necessarily reduce the flow of blood and thus influence the oxygen saturation. Then, the above-described pulse finding algorithm system of the pulse oximeter will generate a "non-pulsatile" alarm. As will be appreciated by those skilled in the art of pulse oximetry, this alarm is not caused by physiological events. Rather, it is caused by the measuring method. Similarly, the inflation of the cuff influences the oxygen saturation. When the measure of oxygen saturation falls below a predetermined threshold, the so-called SaO2-alarm is generated. Further, the inflation of the cuff may influence the measured pulse rate so that same is no longer between predetermined tolerance thresholds which may also cause the generation of an alarm.

U.S. Pat. No. 4,776,339 discloses a patient monitor for measuring The non-invasive blood pressure of the patient and for monitoring the oxygen saturation of the patient's blood. The system comprises an inflatable cuff for disposition about the patient's arm to provide the blood pressure signal and a probe for securement on the finger of the patient to provide the oxygen saturation signal. The system also comprises an alarm circuit to provide a blood pressure alarm signal or an oxygen saturation signal in the event that the actual values of these signals deviate from predetermined acceptable values. A control circuit responds to the inflation of the cuff to feed a signal to the alarm circuit for disabling the oxygen saturation alarm if the cuff is inflated. Although this prior art system overcomes some of the above-mentioned problems of standard pulse oximetry systems, the field of application of the system is somewhat restricted as the alarm circuit requires an input signal indicative of the inflation of the cuff so as to disable the oxygen saturation alarm if the cuff is inflated. On the one hand, the input signal is not available in all systems. On the other hand, the technique also suffers from the problem that it disables more alarms than necessary. For example, dramatical changes in the oxygen saturation may be physiological and not caused by the inflation of the cuff. Therefore, any abrupt changes in the oxygen saturation arising during the inflated condition of the cuff will not be detected by this prior art system.

These problems encountered with the technique described in U.S. Pat. No. 4,776,339 were also recognized by the authors of U.S. Pat. No. 5,253,645 (see column 1, lines 32 to 56 thereof).

However, U.S. Pat. No. 5,253,645 discloses yet another approach for reducing the number of "false" alarms without suppressing relevant alarms. In accordance with the system described in U.S. Pat. No. 5,252,645, the amplitude of the oximeter sensor is compared with a threshold. A signal indicative of an oximeter sensor signal falling below the threshold is fed to a first timer. Further, a blood pressure signal is fed to a second timer. The output signals of both timers are logically combined for generating the audible alarm of the system. An additional visional alarm is created on the mere basis of the output signal of the first mentioned timer. To summarize, this prior art system requires a blood pressure signal and an oximeter sensor signal and derives an alarm by logically combining timer signals derived from these input signals.

In contrast to the above technique, it is the goal of the present invention to analyze an irregular state on the mere basis of an analysis of the spectrophotometric signals.

OBJECT OF THE INVENTION

Accordingly, it is a general object of the invention to provide a method and an apparatus for detecting an irregular state in a non-invasive pulse oximeter system.

It is a further object of the instant invention to provide a method and an apparatus for detecting an irregular state in a non-invasive pulse oximeter system capable of detecting the presence of the irregular state exclusively on the basis of spectrophotometric signals generated by the pulse oximeter system.

It is a further object of the instant invention to provide a method of suppressing a false alarm caused by a non-physiological event in a non-invasive pulse oximeter system.

It is still a further object of the invention to provide an alarm system capable of suppressing a false alarm caused by a non-physiological event in a non-invasive pulse oximeter system.

SUMMARY OF THE INVENTION

In accordance with a first aspect of the invention, these objects are achieved by a method of detecting an irregular state in a non-invasive pulse oximeter system, said system comprising means for generating spectrophotometric signals and oxygen saturation computing means for deriving the arterial hemoglobin oxygen saturation from the spectrophotometric signals, said irregular state detecting method comprising the steps of:

- low pass filtering of the spectrophotometric signal for establishing a low pass filtered spectrophotometric signal;
- high pass filtering of the spectrophotometric signal for establishing a high pass filtered spectrophotometric signal;
- pre-defining at least one criterion for distinguishing between spectrophotometric signals indicative of a normal state of said non-invasive pulse oximeter system and spectrophotometric signals generated by said non-invasive pulse oximeter system when a predetermined non-physiological event occurs, wherein said criterion comprises at least one of the following conditions:
  - the amplitude of the low pass filtered spectrophotometric signal falls in a tolerance interval;
  - the amplitude of the high pass filtered spectrophotometric signal does not exceed a threshold; and
  - the amplitude of the high pass filtered spectrophotometric signal falls within a predetermined transition characteristic;
- judging whether the actual spectrophotometric signals fulfil said at least one pre-defined criterion; and
- detecting the presence of the irregular state if the actual spectrophotometric signals fulfil said at least one pre-defined criterion.

In a preferred embodiment of the invention, said at least one criterion is indicative of the distortion of said spectrophotometric signals caused by said pre-determined non-physiological event.

In a preferred embodiment of the invention, an oxygen saturation probe of said non-invasive pulse oximeter system is disposed on a finger of the patient's arm, and said predetermined non-physiological event is the inflation of a cuff wrapped about the same arm.

In a further preferred embodiment of the invention, said criterion consists in that the following conditions are simultaneously fulfilled:
- the amplitude of the low pass filtered spectrophotometric signal falls in a tolerance interval;
- the amplitude of the high pass filtered spectrophotometric signal does not exceed a threshold;
- the amplitude of the high pass filtered spectrophotometric signal falls within a predetermined transition characteristic; and
- the non-invasive pulse oximeter system generates a non-pulsatile alarm.

In a further preferred embodiment of the invention wherein the non-physiological event is the inflation of a cuff wrapped about the patient's arm, the method further comprises the steps of:
- setting a state machine in a first state if the following conditions are simultaneously fulfilled:
  - the amplitude of the low pass filtered spectrophotometric signal falls in a tolerance interval;
  - the amplitude of the high pass filtered spectrophotometric signal does not exceed a threshold;
  - the amplitude of the high pass filtered spectrophotometric signal falls within a predetermined transition characteristic; and
  - the non-invasive pulse oximeter system generates a non-pulsatile alarm; and
- setting a state machine in a second state when detecting a new pulsation or when a predetermined time has expired after reaching the first state.

In accordance with a second aspect of the invention, these objects are achieved by an apparatus for detecting an irregular state in a non-invasive oximeter system, said system comprising means for generating spectrophotometric signals and oxygen saturation computing means for deriving the arterial hemoglobin oxygen saturation from the spectrophotometric signals, said irregular state detecting apparatus comprising:

- a low pass filter arranged for establishing a low pass filtered spectrophotometric signal;
- a high pass filter arranged for establishing a high pass filtered spectrophotometric signal;
- storing means for storing at least one pre-defined criterion for distinguishing between spectrophotometric signals indicative of a normal state of said non-invasive pulse oximeter system and spectrophotometric signals generated by said non-invasive pulse oximeter system when a predetermined non-physiological event occurs, wherein said criterion comprises at least one of the following conditions:
  - the amplitude of the low pass filtered spectrophotometric signal falls in a tolerance interval;
  - the amplitude of the high pass filtered spectrophotometric signal does not exceed a threshold; and
  - the amplitude of the high pass filtered spectrophotometric signal falls within a predetermined transition characteristic;
- judging means for judging whether the actual photometric signals fulfil said at least one pre-defined criterion; and
- detecting means for detecting the presence of the irregular state if the actual spectrophotometric signals fulfil said at least one pre-defined criterion.

In accordance with a third aspect of the invention, these objects are achieved by a method of suppressing a false alarm caused by a non-physiological event in an non-invasive pulse oximeter system for measuring the arterial hemoglobin oxygen saturation, said non-invasive pulse oximeter system comprising:
- an oxygen saturation sensing probe with light sources for generating light of different wavelengths transmitted through a area of the patient's body and with light detector means for receiving the light of both wavelengths and for generating spectrophotometric signals, a pulse finding means responsive at least one of said spectrophotometric signals for generating a pulse detection signal;

oxygen saturation computing means responsive to said spectrophotometric signals and responsive to said pulse detection signal for deriving diastolic and systolic spectrophotometric signals, for computing relative absorption ratios based on said diastolic and systolic spectrophotometric signals and for computing the arterial oxygen saturation from said relative absorption ratios; and alarm means for generating an alarm if said pulse finding means fails to detect a pulse or if the measured oxygen saturation and/or the measured pulse rate fall out of predetermined tolerance band widths;

said method of suppressing the false alarm comprising the steps of:

low pass filtering of the spectrophotometric signal for establishing a low pass filtered spectrophotometric signal;

high pass filtering of the spectrophotometric signal for establishing a high pass filtered spectrophotometric signal;

pre-defining at least one criterion for distinguishing between spectrophotometric signals indicative of a normal state of said non-invasive pulse oximeter system and spectrophotometric signals generated by said non-invasive pulse ox meter system when a predetermined non-physiological event occurs, wherein said criterion comprises at least one of the following conditions:

the amplitude of the low pass filtered spectrophotometric signal falls in a tolerance interval;

the amplitude of the high pass filtered spectrophotometric signal does not exceed a threshold; and the amplitude of the high pass filtered spectrophotometric signal falls within a predetermined transition characteristic;

judging whether the actual spectrophotometric signals fulfil said at least one pre-defined criterion; and detecting the presence of the irregular state if the actual spectrophotometric signals fulfil said at least one pre-defined criterion, suppressing the alarm generated by said alarm means when detecting the irregular state.

In accordance with a fourth aspect of the invention, these objects are achieved by an alarm system capable of suppressing a false alarm caused by a non-physiological event in an non-invasive pulse oximeter system for measuring the arterial hemoglobin oxygen saturation, said oximeter system comprising:

an oxygen saturation sensing probe with light sources for generating light of different wavelengths transmitted through a area of the patient's body and with light detector means for receiving the light of both wavelengths and for generating spectrophotometric signals, a pulse finding means responsive at least one of said spectrophotometric signals for generating a pulse detection signal;

oxygen saturation computing means responsive to said spectrophotometric signals and responsive to said pulse detection signal for deriving diastolic and systolic spectrophotometric signals, for computing relative absorption ratios based on said diastolic and systolic spectrophotometric signals and for computing the arterial oxygen saturation from said relative absorption ratios; and alarm means for generating an alarm if said pulse finding means fails to detect a pulse or if the measured oxygen saturation and/or the measured pulse rate fall out of predetermined tolerance band widths;

said alarm system suppressing the false alarm comprising:

a low pass filter arranged for establishing a low pass filtered spectrophotometric signal;

a high pass filter arranged for establishing a high pass filtered spectrophotometric signal;

storing means for storing at least one pre-defined criterion for distinguishing between spectrophotometric signals indicative of a normal state of said non-invasive pulse oximeter system and spectrophotometric signals generated by said non-invasive pulse oximeter system when a predetermined non-physiological event occurs, wherein said criterion comprises at least one of the following conditions:

the amplitude of the low pass filtered spectrophotometric signal falls in a tolerance interval;

the amplitude of the high pass filtered spectrophotometric signal does not exceed a threshold; and the amplitude of the high pass filtered spectrophotometric signal falls within a predetermined transition characteristic;

judging means for judging whether the actual photometric signals fulfil said at least one pre-defined criterion;

detecting means for detecting the presence of the irregular state if the actual spectrophotometric signals fulfil said at least one pre-defined criterion; and alarm suppressing means for suppressing the alarm generated by said alarm means when said irregular state detecting apparatus detects the irregular state.

BRIEF DESCRIPTION OF THE DRAWINGS

Other objects and many of the attendant advantages of the present invention will be readily appreciated as same becomes better understood by reference to the following detailed description when considering in connection with the accompanied drawings, in which.

Figure 1:
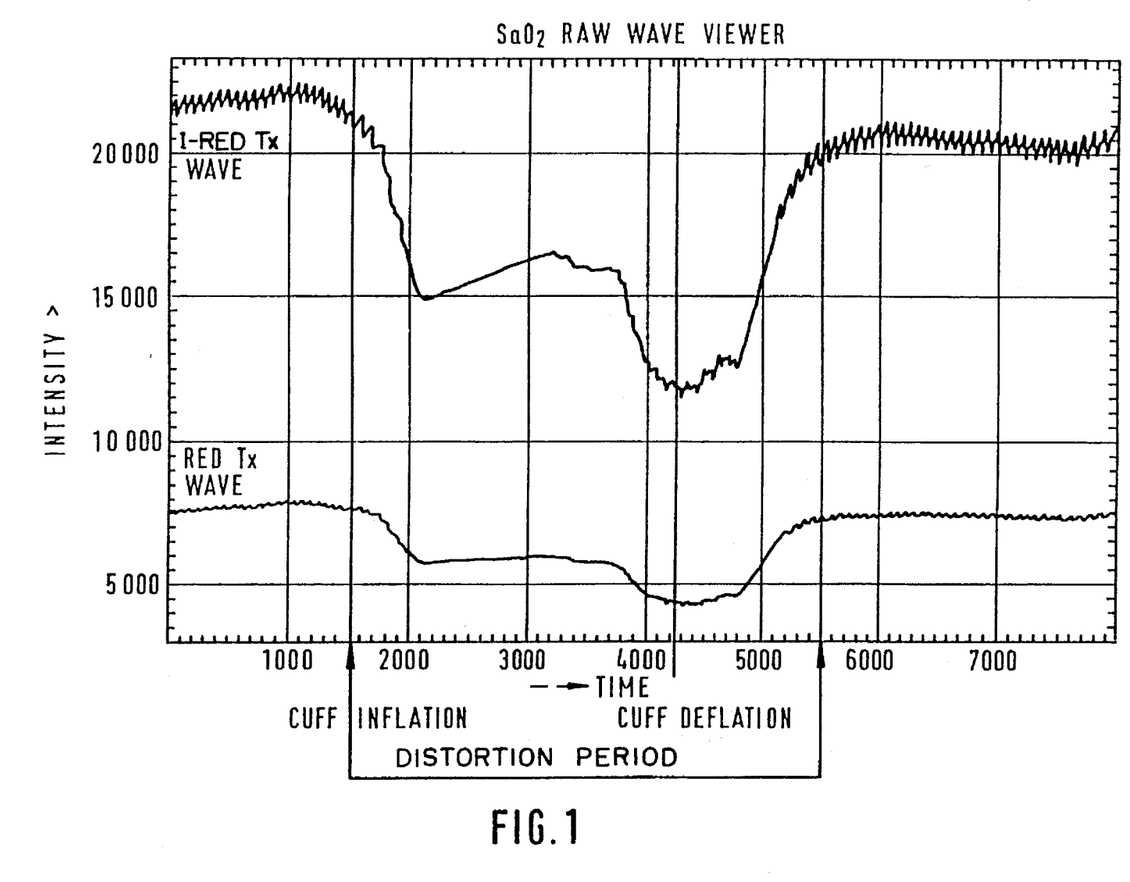
FIG. 1 is a graph of the red and the infrared light absorption signals of a pulse oximeter system, said signals being distorted by the cuff inflation when carrying out a non-invasive blood pressure measurement.

Before explaining the signal interference scenario shown in FIG. 1, it should be noted that the infrared signal wave form and the red signal wave form shown there are generated by the light detector of a oxygen saturation sensing probe of a non-invasive pulse oximeter system for measuring the arterial hemoglobin oxygen saturation. Typically, the oxygen saturation sensing probe of a pulse oximeter system has two different light sources in the form of two light emitting diodes, one emitting light in the red wavelength range and the other one emitting light in the infrared wavelength range, as explained above. The light of both sources is dynamically attenuated by the pulsing blood synchronously with the heartbeat of the patient.

Thus, the spectrophotometric signals generated by the light sensor, which can be implemented by a photodiode, have synchronously pulsing wave forms, as can be seen at the left-hand side of both signal curves before the event "cuff inflation".

As shown in FIG. 1, the cuff inflation causes a distortion of both the red and the infrared light absorption signals or spectrophotometric signals. The distortion is characterized by a rapid change of the pulsatile signal component (AC component) from a normal physiological level to a minimum level when the inflation of the cuff has obstructed the arterial blood flow. As one may further gather from the signal wave forms shown in FIG. 1, the constant signal component (DC component) is only slightly influenced by the artificial or non-physiological external event, namely the inflation of the cuff. After the deflation of the cuff, the signals are recovered to their original status (see FIG. 1), right-hand side of both curves after the event "cuff deflation". It should also be noted that the recovering of the original status requires some time after the event "cuff deflation". Thus, the "distorted time phase" as shown in FIG. 1 starts when inflating the cuff, but is longer than the Time period between the inflation of the cuff and the deflation thereof.

Figure 2:
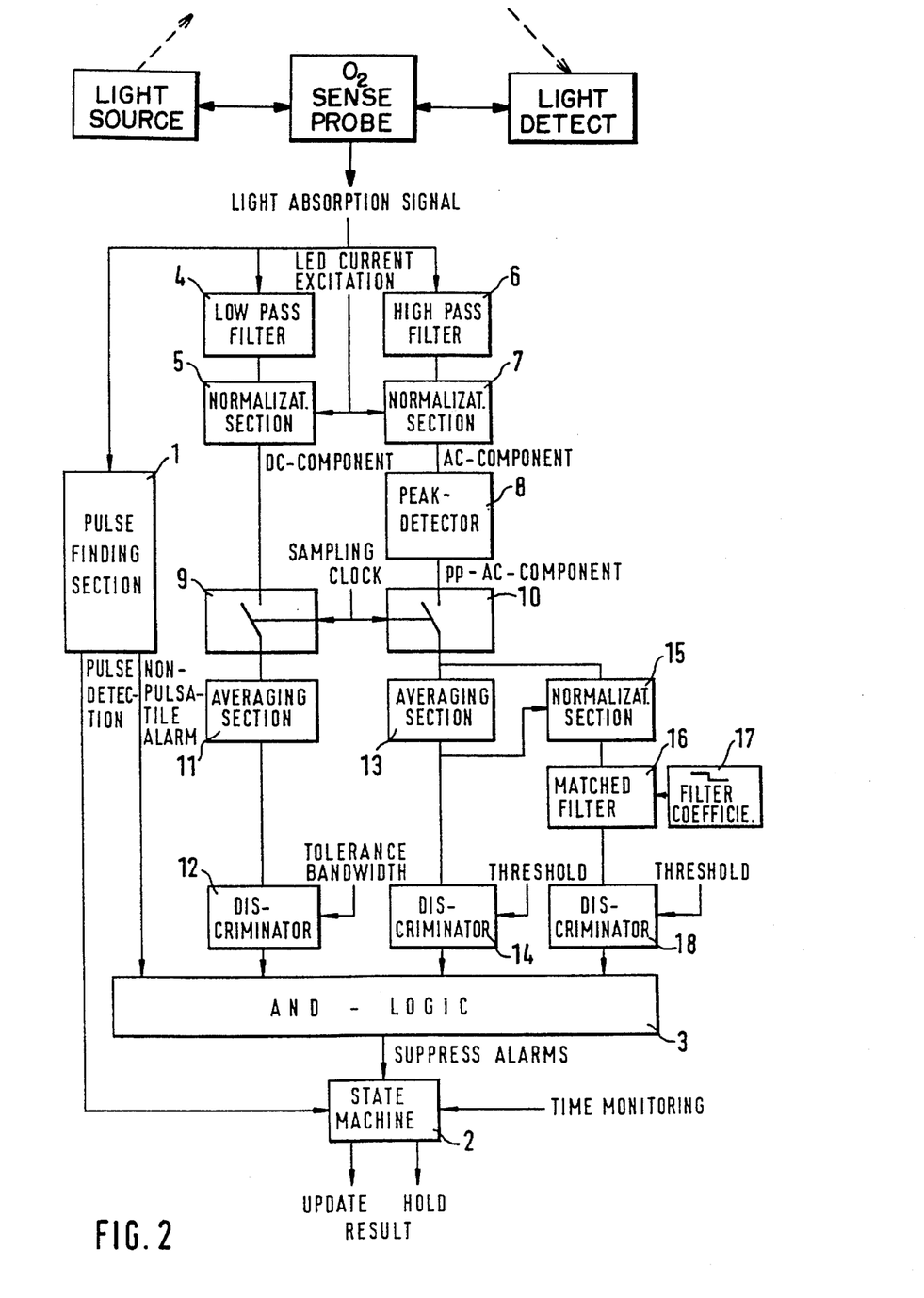
FIG. 2 is a block diagram of a signal analysis for detecting the irregular state of a non-invasive pulse oximeter system in accordance with the invention.

Referring now to FIG. 2, which is a block diagram of the signal analysis for detecting the irregular state, a light absorption signal, i.e. one of the two spectrophotometric signals, is fed To the input of a pulse finding section 1. As it is readily apparent to those having ordinary skill in the field of pulse oximetry, the pulse finding section 1 is typically implemented by a pulse-finding algorithm of the control program of the microcomputer controlling the pulse oximeter. As explained at the beginning, the pulse finding section either generates a pulse detection signal which is fed to a state machine 2 upon detection of a pulse or generates a non-pulsatile alarm signal which is fed to one of four inputs of an AND-logic 3.

Further, the light-absorption signal is fed to a low pass filter 4. The output of the low pass filter 4 is connected to one input of a normalization section 5. A signal indicative of the excitation current fed to the light emitting diodes is fed to the other input of the normalization section 5. Thus, the output of the normalization section 5 is the normalized DC-component of the light-absorption signal. Similarly, the light-absorption signal is also fed to a high pass filter 6, the output of which is connected to one input of a further normalization section 7. The signal indicative of the excitation of the LED current is also fed to the other input of this normalization section 7. As a consequence, the output of said normalization section 7 represents a normalized AC-component of the light absorption signal.

A peak detector 8 holds the peaks of the normalized AC-component of the light absorption signal. Both the output of the first-mentioned normalization section 5 and the output of the peak detector 8 are periodically sampled by respective sampling sections 9, 10, both of which having a sampling port to which a sampling clock is fed. The output of the first-mentioned sampling section 9 is fed to a first averaging section 11, the output of which is connected to the input of a discriminator 12 defining a tolerance band width. Thus, the output of discriminator 12 is "high" if the averaged normalized DC-component of the light absorption signal falls in said tolerance band width.

Similarly, the output of the second-mentioned sampling section 10 is fed to a second averaging section 13, the output of which is connected to a second discriminator 14.

The discriminator 14 generates an output signal of "high" logic level if the averaged peak amplitudes of the AC-component of the light absorption signal does not exceed a predetermined threshold.

Further, the output of the second-mentioned sampling section 10 is fed to one input of a third normalization section 15, wherein the other "referenced" input of this third normalization section 15 is connected to the output of the second averaging section 13. Thus, the output of the third normalization section 15 is indicative of the relative level of the AC-peak-component. This signal is applied to the input of a matched filter 16 which is programmed with the inverse sequence of time samples of the transient of the normalized pulsatile signal component (AC) as matched filter coefficients. The matched filter coefficients are supplied by a filter coefficient section 17. Thus, the output of the matched filter 16 is indicative of the transition of the AC components of the light absorption signal.

A third discriminator 18 compares the output of the matched filter 16 with a predetermined threshold to generate a corresponding logic output. The AND-logic 3 logically combines the non-pulsatile alarm signal as generated by the pulse finding section 1 and the respective outputs of the first, second and third discriminators 12, 14 and 18 for generating a suppressed alarm signal, which is fed to the above-mentioned state machine 2. Further, a time monitoring signal which is "high" after reaching a time out in the suppress alarms state of the state machine 2 forms another input of the state machine. The state machine 2 causes the system to hold the last oxygen saturation values as long as it receives the suppressed alarm signal. Otherwise, the values of the arterial hemoglobin oxygen saturation will be updated.

Figure 3:
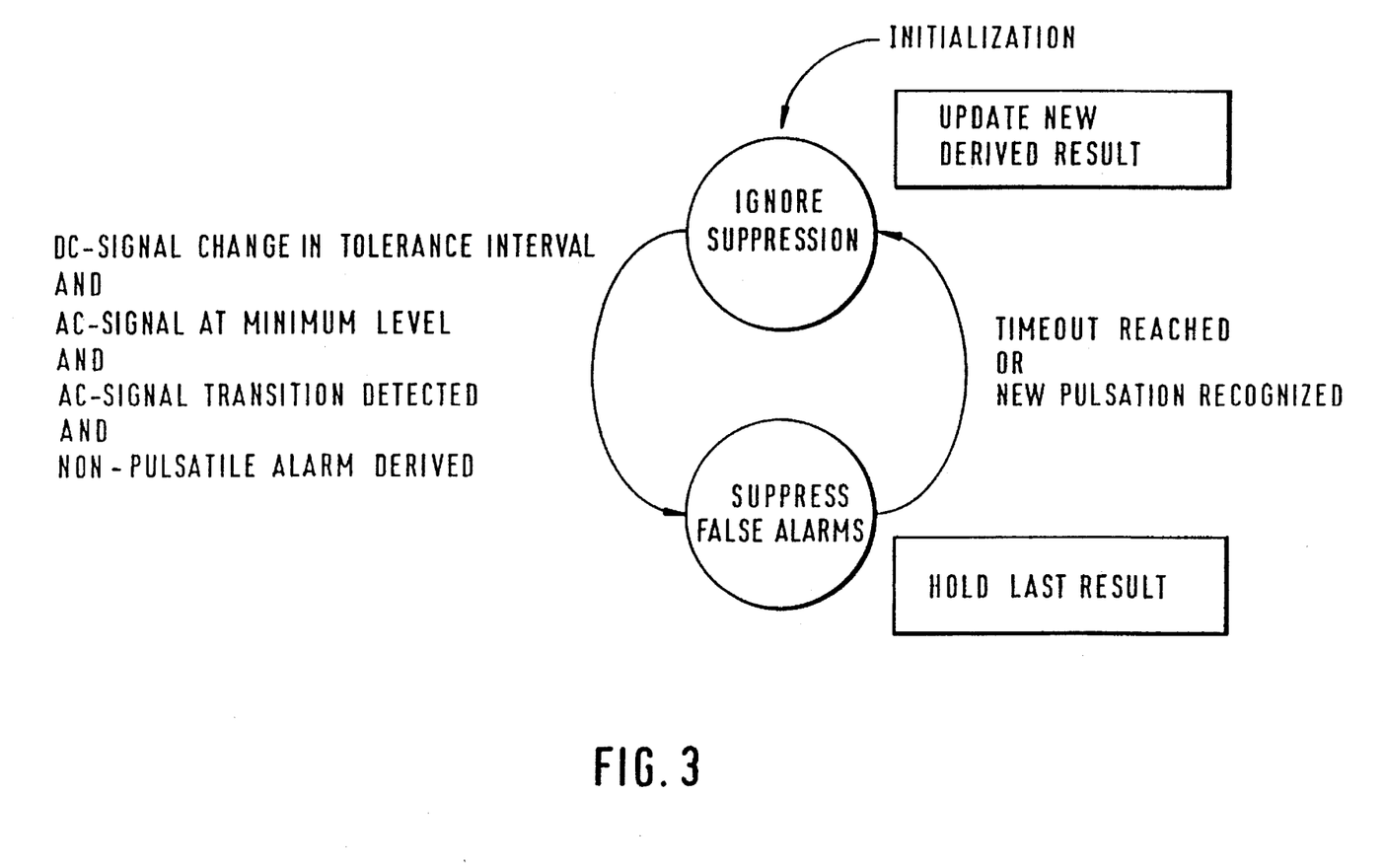
FIG. 3 is a state diagram of the state machine of a preferred embodiment of the invention.

The above-described mode of operation of the "intelligent" system of the invention can also be defined in terms of the conditions and states of a state machine as shown in FIG. 3. The state machine in accordance with FIG. 3 represents the two states "Ignore suppression" and "Suppress false alarms". Upon initialization of the system, the system assumes its first state "Ignore suppression". A change from this first state "Ignore suppression" to the second state "Suppress false alarms" is effected only if the following four conditions are fulfilled:

The DC signal changes are within the tolerance interval;

The AC signal does not exceed a minimum threshold;

An AC signal transition has been detected; and

The non-pulsatile alarm is present.

The conditions for changing from this second state "Suppress false alarms" to the first state "Ignore suppression" are either the reaching of a time out in the second condition, which means that the entering into the second state is more than a predetermined period time ago, or that a new valid pulsation has been recognized by the pulse finding section 4.

In the first state "Ignore suppression", a continuous updating of the derived results, i.e. of the hemoglobin oxygen saturation values, is carried out. In the second state "Suppress false alarms" the last results, i.e. the last validly derived hemoglobin oxygen saturation values, are held.

Naturally, the respective oxygen saturation values can be displayed. Further, the state of the state machine can also be displayed.

Figure 4:
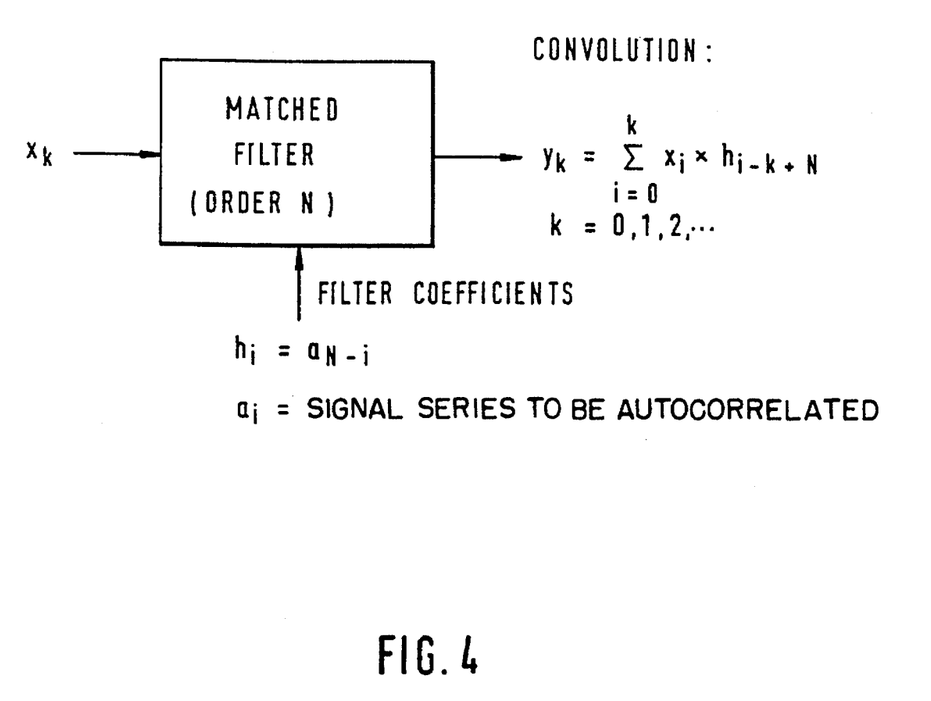
FIG. 4 is a block diagram of the matched filter shown in FIG. 2.
Figure 5A:
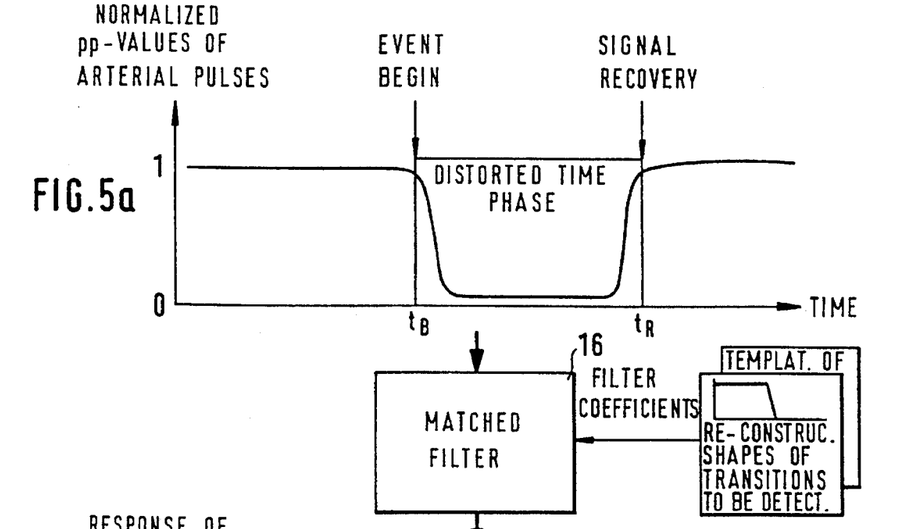
FIGS. 5a, 5b and 5c are graphs of signals appearing at the input and output of the matched filter and the discriminator shown in FIG. 2.

One key element of this invention is the detection of predefined significant transients in the pulsatile signal component (pp-AC-Component). There are kind of transients which are characteristic to the original cause of specific events, typically influenced by external artificial impacts. In the above preferred embodiment, such a transient detection is performed by means of the matched filter 16. The pulsatile signal component (see FIG. 5a)is passed through the normalization section 15 which outputs a scaled pp-signal relative to the time averaged signal itself. That normalized pp-signal is directly reflecting changes in the pulse amplitude relative to it's past tendency. This signal is then delivered to the input of the matched filter 15 for detecting specific transients. The matched filter 15 is designed such that it responds with a maximum output signal if a specific signal is delivered to the filter's input. Therefore it can be used as a kind of autocorrelator, adapted for a specific signal. The most convenient realization of such a matched filter is the implementation as a time discrete digital filter. To achieve the filter property of signal matching it is necessary to program the filter coefficients with a sequence which is inverse with respect to the time with regard to a series of samples of the signal for which the matching is desired. If N is defined as the order of the filter, it is a normal behavior of the matched filter that the response is delayed by N discrete time cycles. FIG. 4 shows the basic definition of the time discrete matched filter 16.

The interesting transients must be analyzed and predetermined. All these transients can be stored as time discrete sets of sample sequences in a template. Then the matched filter 16 with the order N can be designed by programming it with N-coefficients by effecting an inversion with respect to the time of the transient consisting of the sequence of N time discrete samples. The performing of the filter operation is a standard convolution calculation.

Figure 5B:
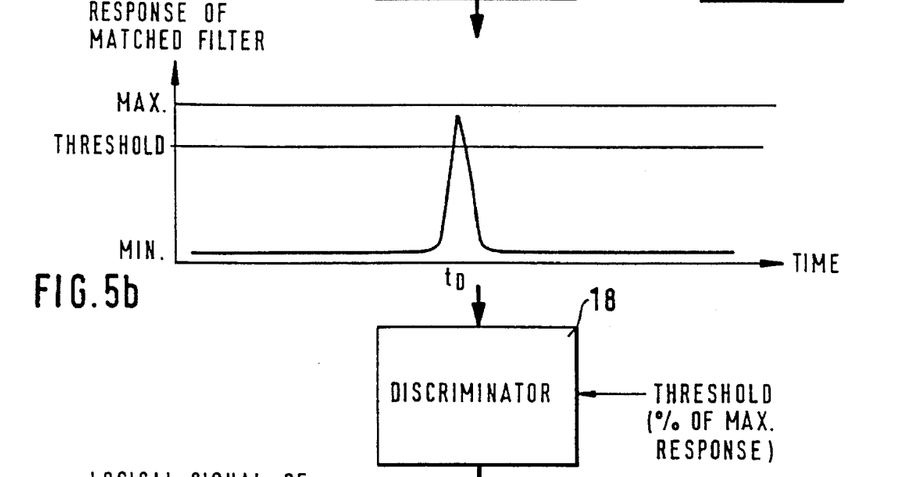
Figure 5C:
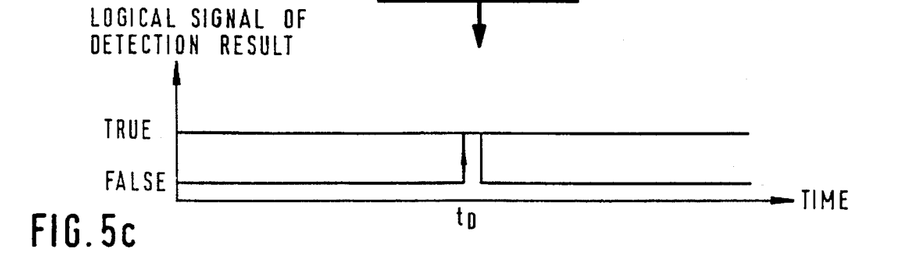

This transient analysis also offers the possibility to analyze different and independent classes of characteristic transients by matched filtering. This can be done easily through defining further sets of filter coefficients as mentioned above, each of it describing a separate shape of a signal transition, for which the matched filter provides a maximum sensibility. That means the system responds with the maximum output signal if one of these defined transient shapes are processed. Furthermore, each detected transient can be identified and correlated to the specific source of cause. The output signal of the matched filter (see FIG. 5b) is then compared with a predefined or adaptive threshold in the discriminator 18. The discriminator 18 delivers a logical signal (see FIG. 5c). This signal can be used for further processing.

I claim:

1. A method of detecting an irregular state in a non-invasive pulse oximeter system, said system comprising means for generating a spectrophotometric signal, and oxygen saturation computing means for deriving arterial hemoglobin oxygen saturation from the spectrophotometric signal, said method comprising the steps of:

low pass filtering said spectrophotometric signal to establish a low pass filtered spectrophotometric signal;

high pass filtering the spectrophotometric signal to establish a high pass filtered spectrophotometric signal;

determining if conditions a–d, as recited hereafter, are simultaneously fulfilled:

(a) an amplitude of the low pass filtered spectrophotometric signal falls in a tolerance interval;

(b) an amplitude of the high pass filtered spectrophotometric signal does not exceed a threshold;

(c) said amplitude of the high pass filtered spectrophotometric signal falls within a predetermined transition characteristic; and (d) a non-pulsatile alarm is generated by said non-invasive pulse oximeter system;

signalling a presence of an irregular state indicative of a predetermined non-physiological event if the spectrophotometric signal fulfills all said conditions.

2. The method as set forth in claim 1, further comprising: disposing an oxygen saturation probe of said non-invasive pulse oximeter system on a finger of a patient's arm, and wherein an inflation of a blood pressure cuff wrapped about said patient's arm causes said irregular state.

3. The method as set forth in claim 1, wherein the non-physiological event results from an inflation of a cuff wrapped about a patient's arm and wherein the method further comprises the steps of:

setting a state machine in a first state if conditions hereafter recited are simultaneously fulfilled:

said amplitude of the low pass filtered spectrophotometric signal falls in the tolerance interval;

said amplitude of the high pass filtered spectrophotometric signal does not exceed the threshold;

said amplitude of the high pass filtered spectrophotometric signal falls within the predetermined transition characteristic; and the non-invasive pulse oximeter system generates the non-pulsatile alarm; and setting said state machine in a second state when detecting a new pulsation or when a predetermined time has expired after being set in the first state.

4. An apparatus for detecting an irregular state in a non-invasive oximeter system, said system comprising means for generating a spectrophotometric signal, and oxygen saturation computing means for deriving arterial hemoglobin oxygen saturation from the spectrophotometric signal, said irregular state detecting apparatus comprising:

low pass filter means for establishing a low pass filtered spectrophotometric signal from said spectrophotometric signal;

a high pass filter means for establishing a high pass filtered spectrophotometric signal from said spectrophotometric signal;

storing means for storing conditions for distinguishing between a spectrophotometric signal indicative of a normal state and a spectrophotometric signal generated by said non-invasive pulse oximeter system when a predetermined non-physiological event occurs, the conditions being as follows:

an amplitude of the low pass filtered spectrophotometric signal falls in a tolerance interval;

an amplitude of the high pass filtered spectrophotometric signal does not exceed a threshold; and said amplitude of the high pass filtered spectrophotometric signal falls within a predetermined transition characteristic;

judging means responsive to at least said low pass filtered spectrophotometric signal, said high pass filtered spectrophotometric signal and said conditions, for judging whether said spectrophotometric signal fulfills said conditions; and means for signalling a presence of an irregular state indicative of a predetermined non-physiological event if said spectrophotometric signal fulfills said conditions.

5. In a non-invasive pulse oximeter system for measuring the arterial hemoglobin oxygen saturation and for performing a method of suppressing a false alarm caused by a non-physiological event, said non-invasive pulse oximeter system comprising:

an oxygen saturation sensing probe with light source means for generating light of different wavelengths transmitted through an area of a patient's body and with light detector means for receiving light of the different wavelengths and for generating a spectrophotometric signal;

a pulse finding means responsive to said spectrophotometric signal for generating a pulse detection signal;

oxygen saturation computing means responsive to said spectrophotometric signal and responsive to said pulse detection signal, for deriving a diastolic spectrophotometric signal and a systolic spectrophotometric signal, for computing relative absorption ratios based on said diastolic spectrophotometric signal and said systolic spectrophotometric signal and for computing arterial oxygen saturation from said relative absorption ratios; and alarm means for generating an alarm if said pulse finding means fails to detect a pulse or if a measured arterial oxygen saturation and/or a measured patient pulse rate fall outside of a predetermined tolerance band width;

means for low pass filtering of the spectrophotometric signal for establishing a low pass filtered spectrophotometric signal;

means for high pass filtering of the spectrophotometric signal for establishing a high pass filtered spectrophotometric signal;

means for judging whether the spectrophotometric signal simultaneously fulfills the following conditions;

an amplitude of the low pass filtered spectrophotometric signal falls in a tolerance interval;

an amplitude of the high pass filtered spectrophotometric signal does not exceed a threshold;

said amplitude of the high pass filtered spectrophotometric signal falls within a predetermined transition characteristic; and a non-pulsatile alarm is generated by said alarm means;

means for signalling a presence of an irregular state indicative of a predetermined non-physiological event if the spectrophotometric signal fulfills said conditions and suppressing the alarm generated by said alarm means upon the presence of said irregular state.

6. An alarm system for suppressing a false alarm caused by a non-physiological event in a non-invasive pulse oximeter system for measuring arterial hemoglobin oxygen saturation, said pulse oximeter system comprising:

oxygen saturation sensing probe means with light source means for generating light of different wavelengths transmitted through an area of the patient's body and with light detector means for receiving light of the different wavelengths and for generating a spectrophotometric signal;

a pulse finding means responsive to said spectrophotometric signal for generating a pulse detection signal;

oxygen saturation computing means responsive to said spectrophotometric signal and responsive to said pulse detection signal, for deriving a diastolic spectrophotometric signal and a systolic spectrophotometric signal, for computing relative absorption ratios based on said spectrophotometric diastolic signal and said systolic spectrophotometric signal and for computing arterial oxygen saturation from said relative absorption ratios; and alarm means for generating an alarm if said pulse finding means fails to detect a pulse or if a measured arterial oxygen saturation and/or a measured pulse rate fall out of predetermined tolerance band widths;

said alarm means including means for suppressing the false alarm comprising:

a low pass filter for establishing a low pass filtered spectrophotometric signal from a spectrophotometric signal;

a high pass filter for establishing a high pass filtered spectrophotometric signal from a spectrophotometric signal;

storing means for storing conditions for distinguishing between a spectrophotometric signal indicative of a normal state of said non-invasive pulse oximeter system and a spectrophotometric signal generated by said non-invasive pulse oximeter system when a predetermined non-physiological event occurs, the conditions being as follows:

an amplitude of the low pass filtered spectrophotometric signal falls in a tolerance interval;

an amplitude of the high pass filtered spectrophotometric signal does not exceed a threshold;

said amplitude of the high pass filtered spectrophotographic signal falls within a predetermined transition characteristic;

said non-invasive pulse oximeter system generates a non-pulsatile alarm;

judging means for judging whether said spectrophotometric signal fulfills all said conditions;

means for signalling a presence of an irregular state indicative of a predetermined non-physiological event if said spectrophotometric signal fulfills all said conditions; and alarm suppressing means for suppressing an alarm generated by said alarm means.

* * * * *

UNITED STATES PATENT AND TRADEMARK OFFICE
CERTIFICATE OF CORRECTION

PATENT NO. : 5,517,988
DATED : May 21, 1996
INVENTOR(S) : Gerhard Klamser

It is certified that error appears in the above-indentified patent and that said Letters Patent is hereby corrected as shown below:

On the title page, item [75] Inventor name should read --Gerhard

Klamser--.

Column 11, between lines 25 and 26, insert --means for performing a method of suppressing a false alarm, further comprising--.

Signed and Sealed this

Fifth Day of November, 1996

Attest:

BRUCE LEHMAN

*Attesting Officer*     *Commissioner of Patents and Trademarks*